US012766341B2

(12) United States Patent
Yoshida et al.

(10) Patent No.: US 12,766,341 B2
(45) Date of Patent: Oct. 20, 2026

(54) MULTILEAF COLLIMATOR AND RADIATION THERAPY DEVICE

(71) Applicants: Hitachi High-Tech Corporation, Tokyo (JP); MITSUBISHI HEAVY INDUSTRIES MACHINERY TECHNOLOGY CORPORATION, Hiroshima (JP)

(72) Inventors: Koki Yoshida, Tokyo (JP); Takashi Ishizuka, Tokyo (JP); Satoshi Arai, Hiroshima (JP)

(73) Assignees: HITACHI HIGH-TECH CORPORATION, Tokyo (JP); MITSUBISHI HEAVY INDUSTRIES MACHINERY TECHNOLOGY CORPORATION, Tokyo (JP)

( * ) Notice: Subject to any disclaimer, the term of this patent is extended or adjusted under 35 U.S.C. 154(b) by 159 days.

(21) Appl. No.: 18/689,106

(22) PCT Filed: Feb. 6, 2023

(86) PCT No.: PCT/JP2023/003728
§ 371 (c)(1),
(2) Date: Mar. 5, 2024

(87) PCT Pub. No.: WO2023/149569
PCT Pub. Date: Aug. 10, 2023

(65) Prior Publication Data

US 2024/0399171 A1 Dec. 5, 2024

(30) Foreign Application Priority Data

Feb. 7, 2022 (JP) ................................ 2022-017085

(51) Int. Cl.
*A61N 5/10* (2006.01)
*G21K 1/04* (2006.01)

(52) U.S. Cl.
CPC .......... *A61N 5/1045* (2013.01); *G21K 1/046* (2013.01)

(58) Field of Classification Search
None
See application file for complete search history.

(56) References Cited

U.S. PATENT DOCUMENTS

2007/0262274 A1 11/2007 Creed et al.
2013/0000308 A1 1/2013 Humphrey
(Continued)

FOREIGN PATENT DOCUMENTS

CN 207186926 U 4/2018
EP 3 827 882 A1 6/2021
(Continued)

OTHER PUBLICATIONS

International Search Report PCT/JP2023/003728 Apr. 18, 2023.
Extended European Search Report received in corresponding European Application No. 23749885.2 dated Nov. 24, 2025.

*Primary Examiner* — Hoon K Song
(74) *Attorney, Agent, or Firm* — MATTINGLY & MALUR, PC

(57) ABSTRACT

An object of the invention is to obtain a position of each leaf with high accuracy by a configuration that is easy to be manufactured in a multileaf collimator. The multileaf collimator includes a plurality of leaves, and a reflection surface that reflects light emitted from a light source is formed on a peripheral end surface, other than a collimated end surface a, among surrounding end surfaces of the leaf. The peripheral end surface includes a longitudinal end surface d opposite to the collimated end surface a, and an upper lateral end surface b extending from one end of the longitudinal end surface d toward the collimated end surface a. The reflection
(Continued)

surface may be a region where the peripheral end surface is subjected to reflection processing.

12 Claims, 12 Drawing Sheets

(56) References Cited

U.S. PATENT DOCUMENTS

2016/0325117 A1 11/2016 Arai
2016/0325118 A1* 11/2016 Arai ........................ G21K 1/046
2021/0106845 A1* 4/2021 Liu .......................... A61B 6/06

FOREIGN PATENT DOCUMENTS

JP 2010-104452 A 5/2010
WO 2015/107660 A1 7/2015

* cited by examiner

[FIG. 1]
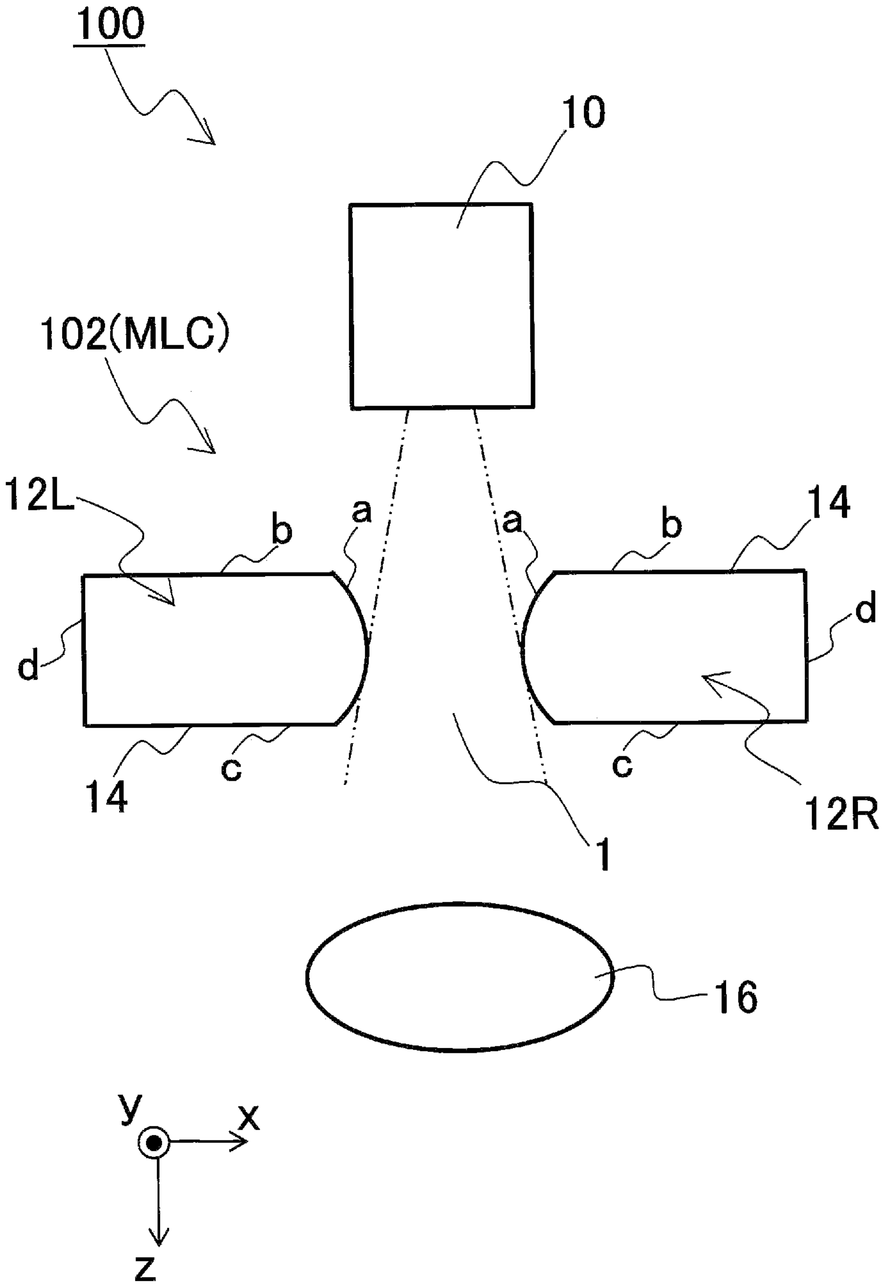

[FIG. 2]
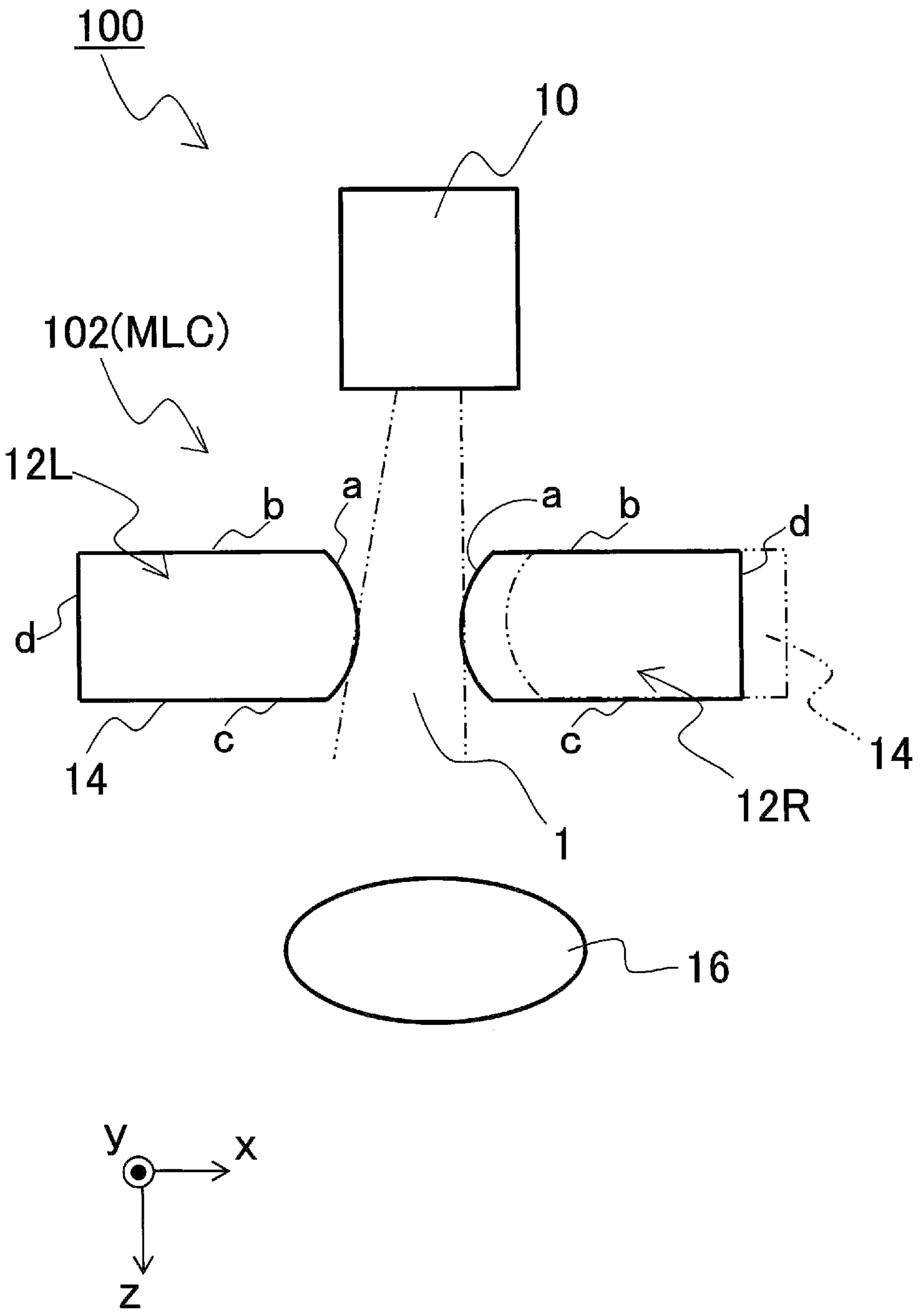

[FIG. 3]
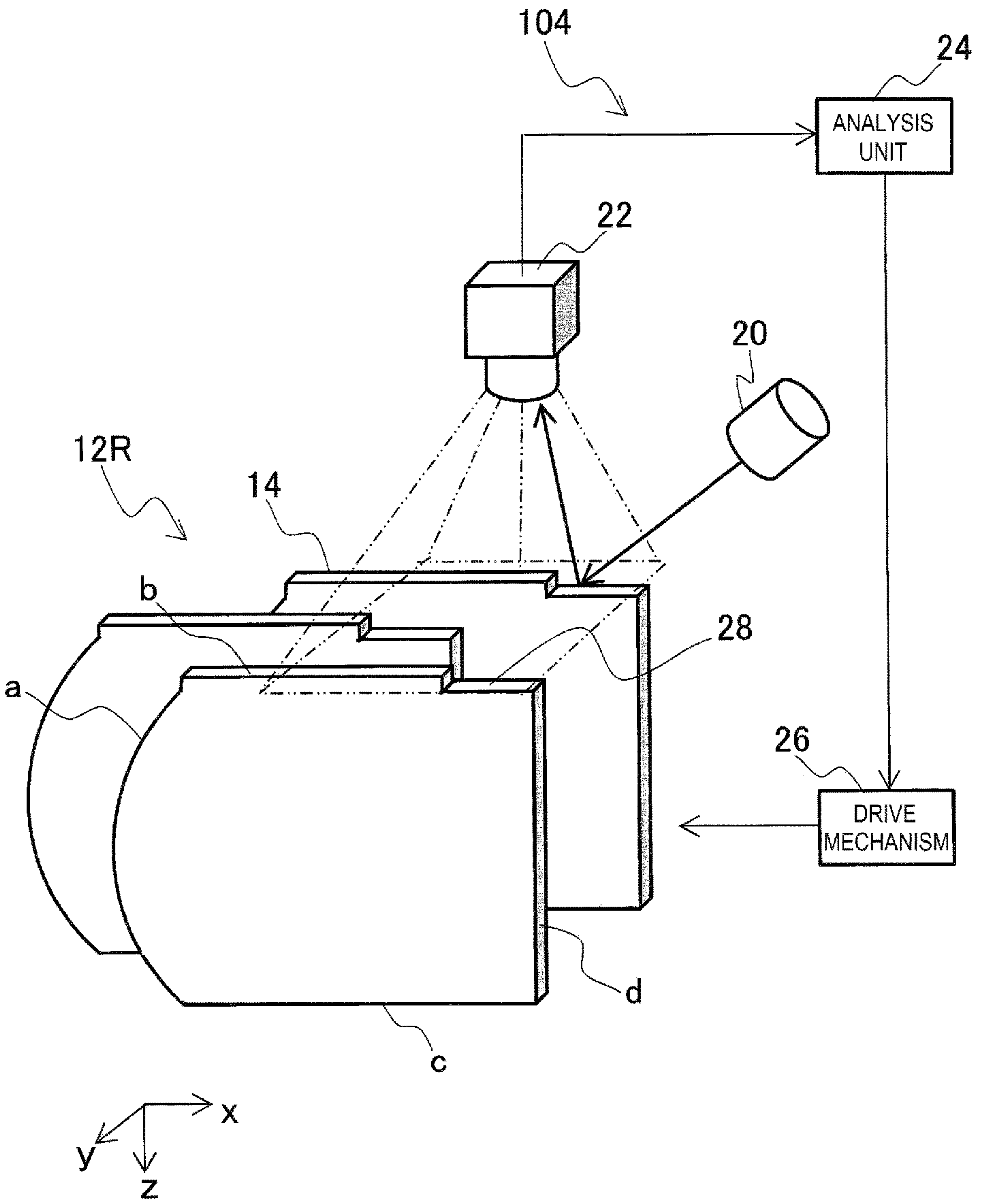

[FIG. 4]
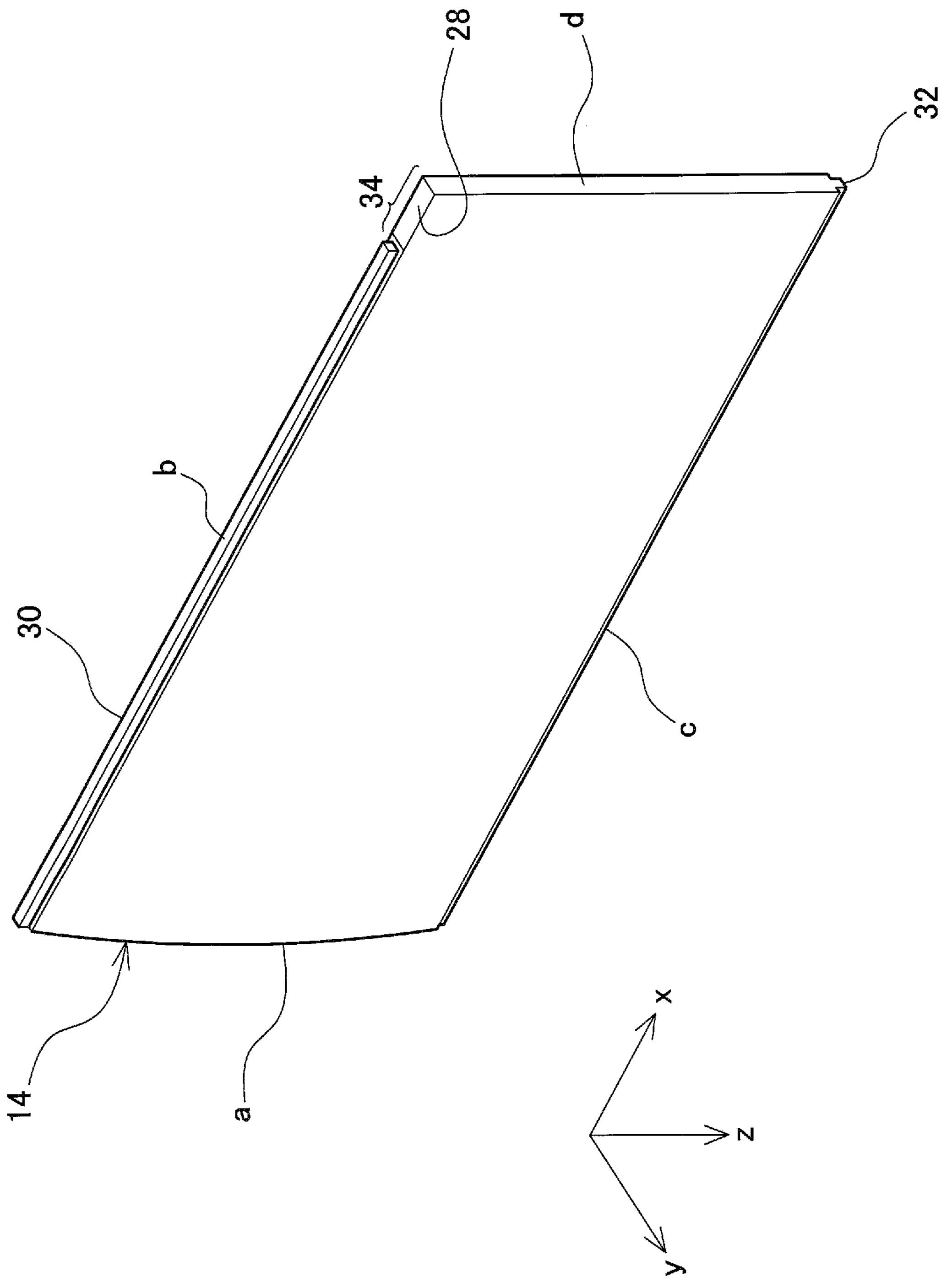

[FIG. 5]
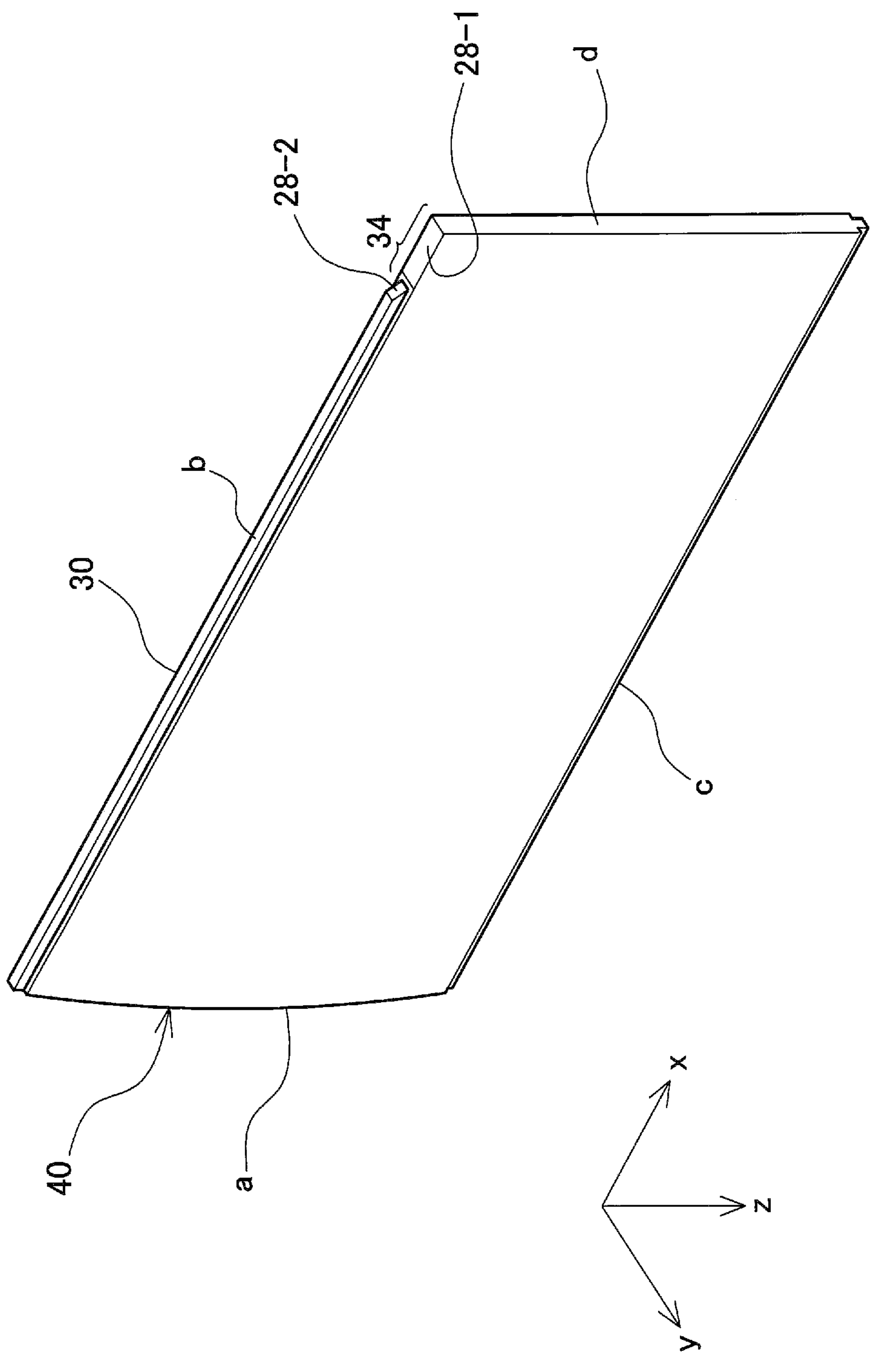

[FIG. 6]
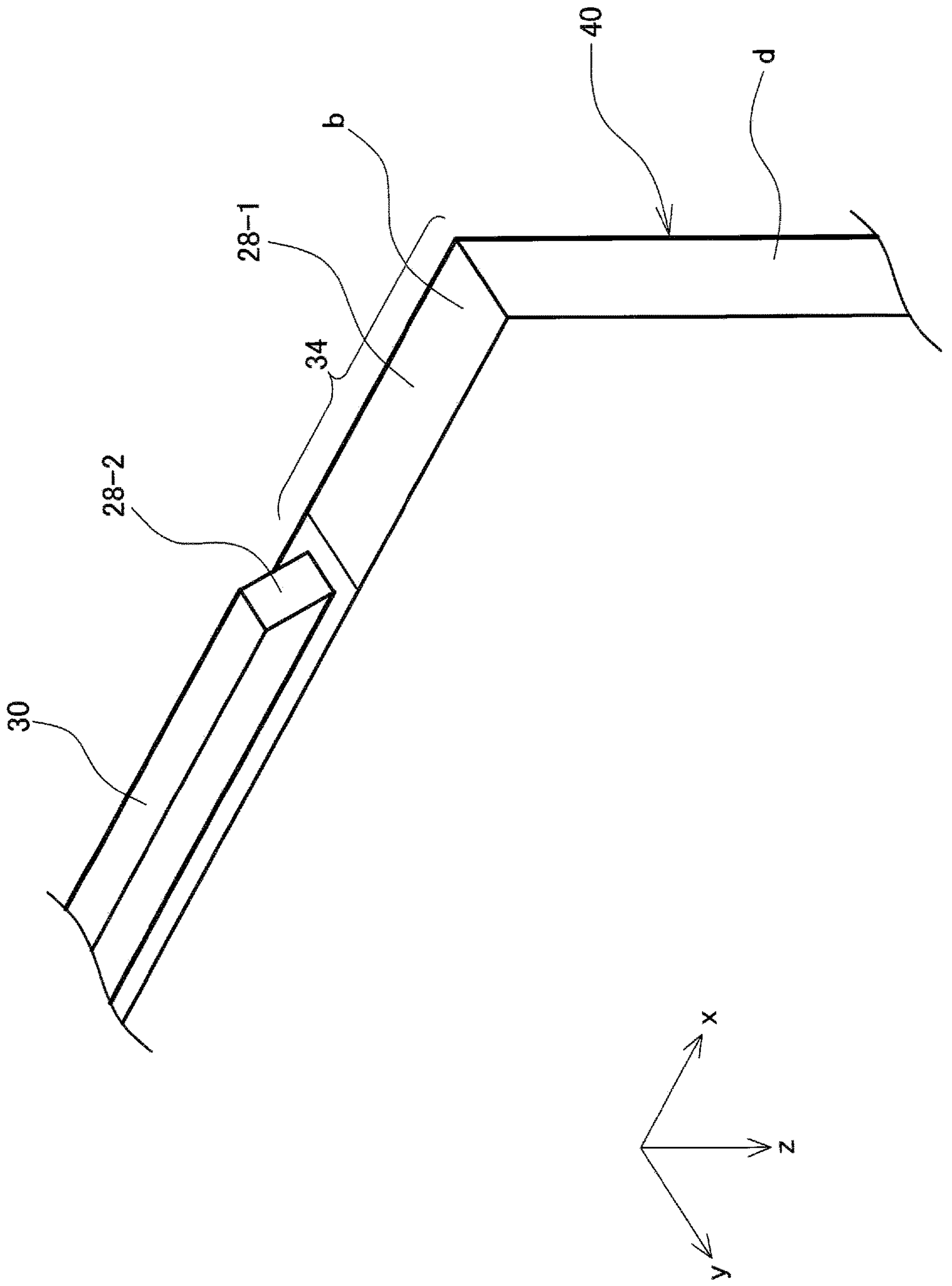

[FIG. 7]
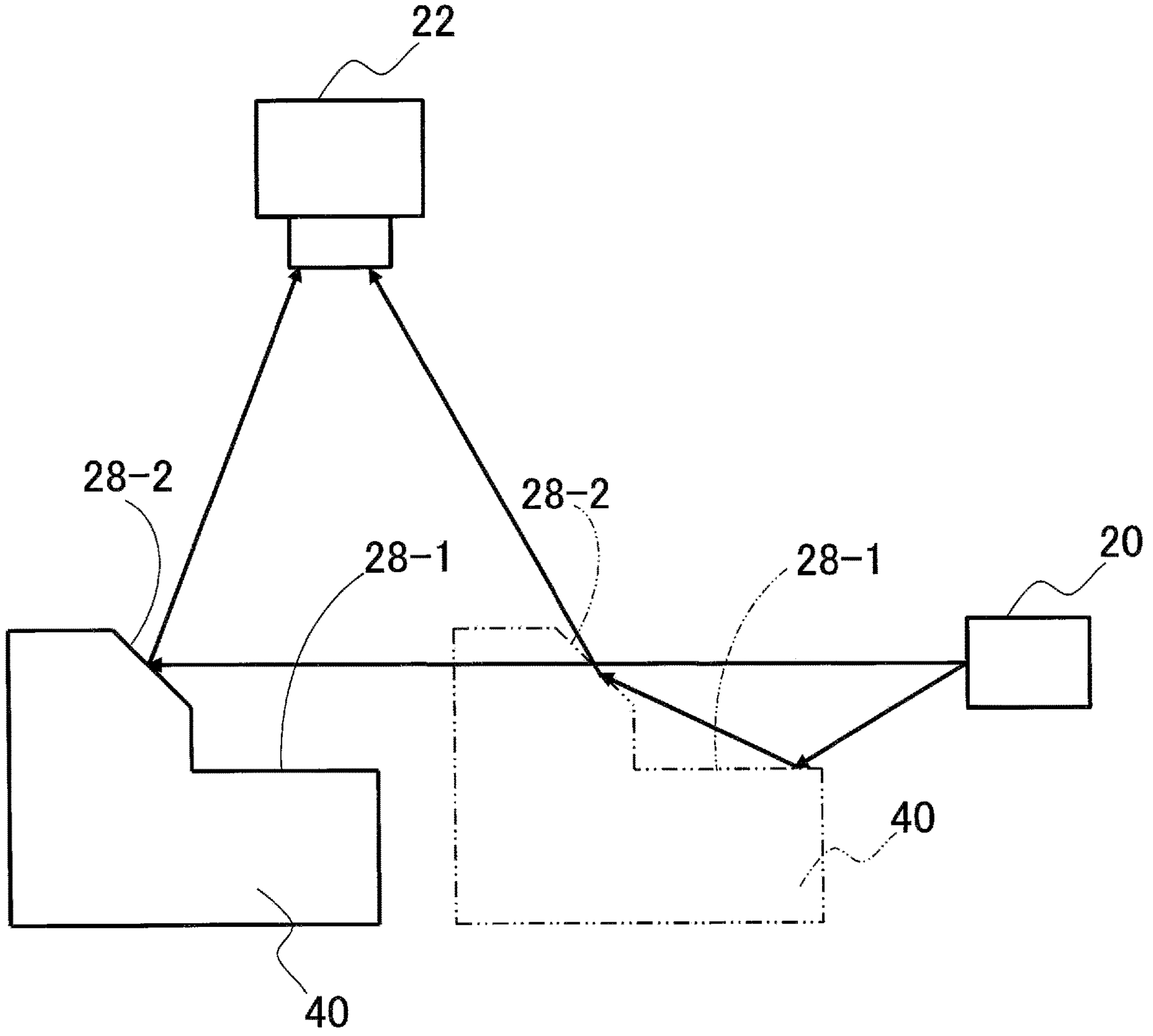

[FIG. 8]
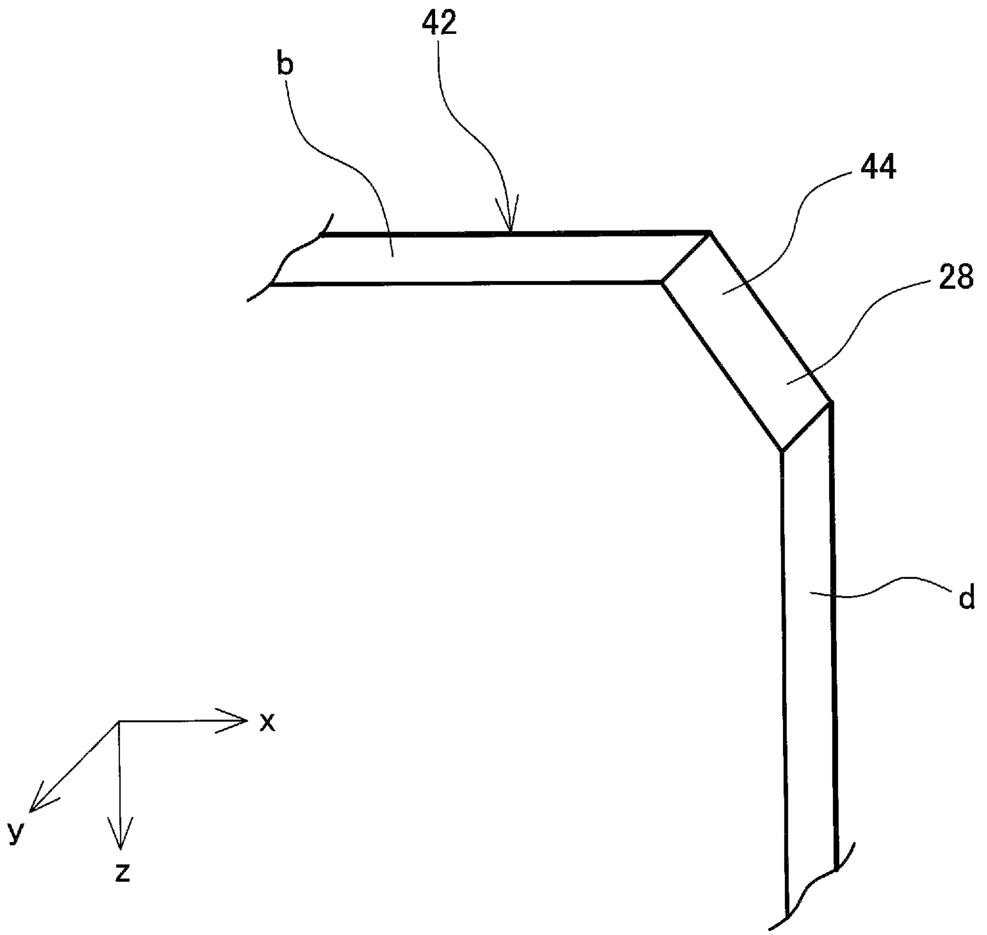

[FIG. 9]
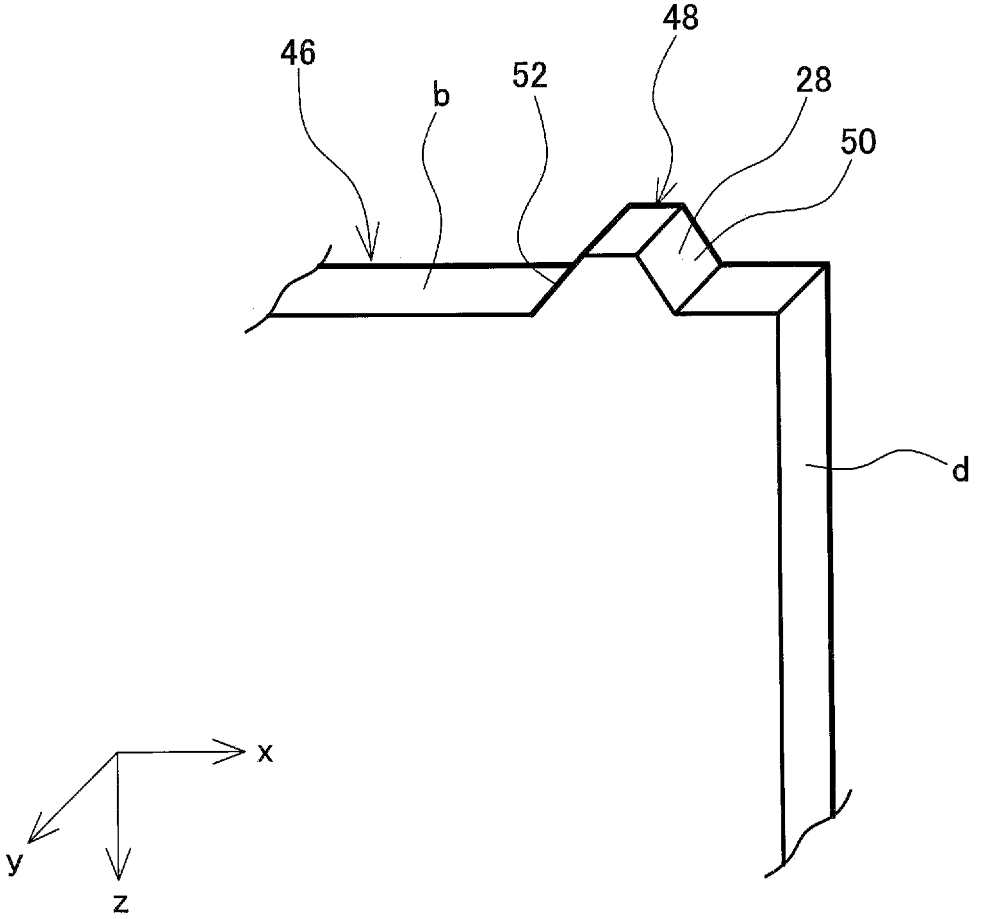

[FIG. 10]
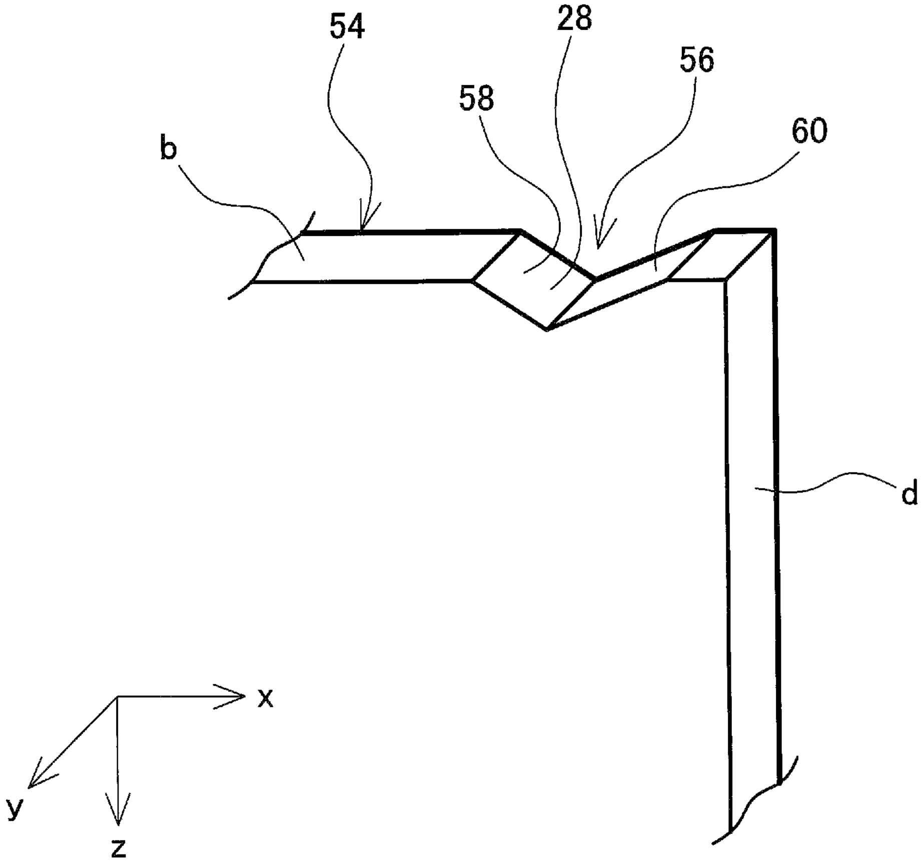

[FIG. 11]
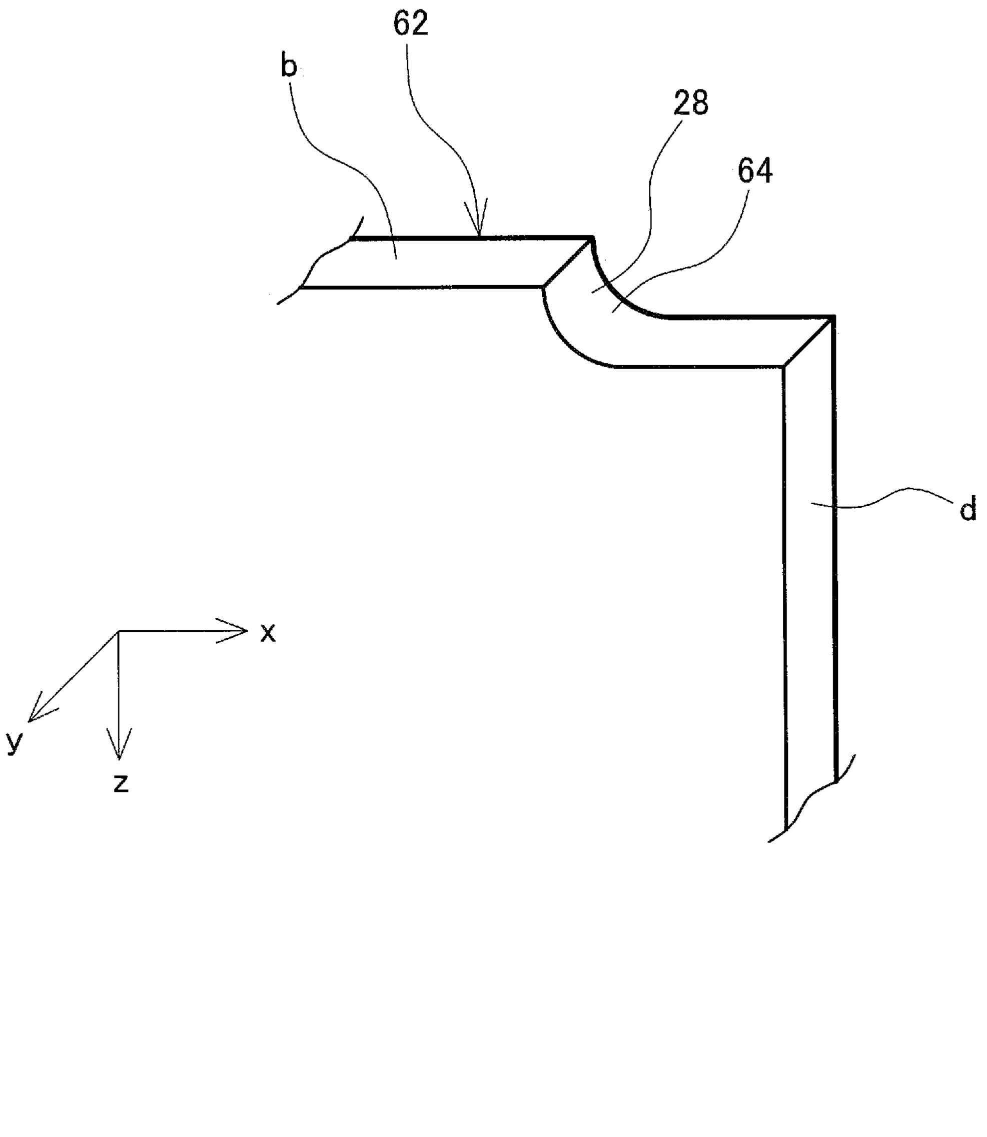

[FIG. 12]
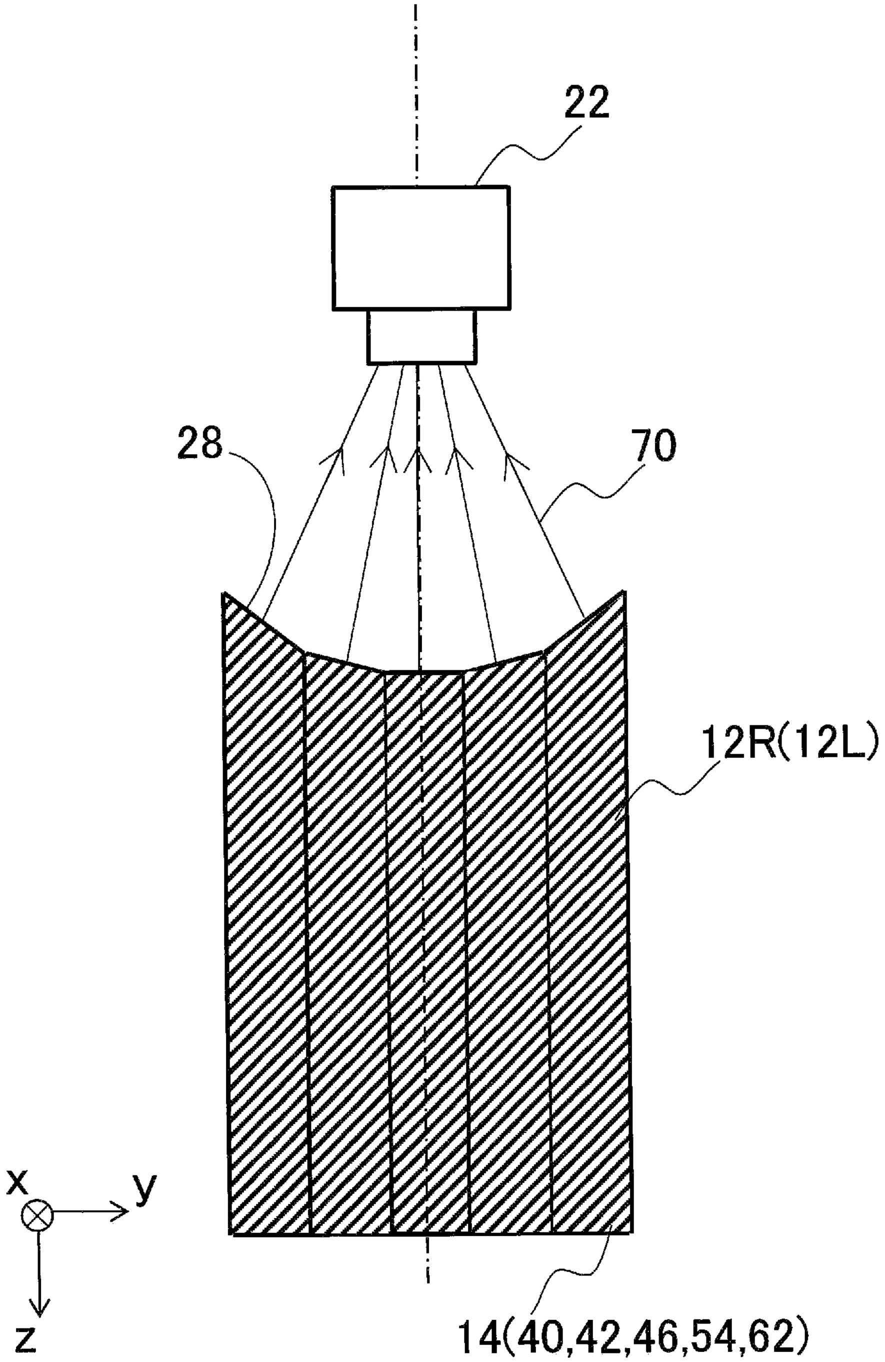

MULTILEAF COLLIMATOR AND RADIATION THERAPY DEVICE

TECHNICAL FIELD

The present invention relates to a multileaf collimator and a radiation therapy device, and more particularly, to a leaf structure of the multileaf collimator.

BACKGROUND ART

A radiation therapy device is widely used. The radiation therapy device treats an affected part by irradiating the affected part with radiation rays. In order to limit a region irradiated with radiation rays to the affected part, the radiation therapy device includes a multileaf collimator.

The multileaf collimator includes a pair of leaf assemblies disposed to face each other. Each leaf assembly includes a plurality of leaves stacked in a thickness direction. The leaf is a plate-like member formed of a material that does not transmit radiation rays. The pair of leaf assemblies are disposed such that end surfaces of the plurality of leaves belonging to one leaf assembly face end surfaces of the plurality of leaves belonging to the other leaf assembly. A passage region through which the radiation rays pass is formed between the pair of leaf assemblies.

By changing a position along a surface direction of the leaf belonging to the leaf assembly, a shape and a size of the passage region are adjusted. A shape (cross-sectional shape) of the radiation rays in a cross section perpendicular to a traveling direction and spread of the radiation rays are adjusted according to the shape and the size of the passage region.

In order to adjust the position of the leaf along the surface direction, the radiation therapy device includes a drive mechanism that moves the leaf along the surface direction. In the radiation therapy device, the position of the leaf is detected, and the position of the leaf is adjusted by the drive mechanism such that the position of the leaf is an appropriate position.

The following PTLs 1 to 3 describe multileaf collimators. PTL 1 describes the multileaf collimator in which each leaf is provided with a marker portion. The marker portion is marked with a recognition mark by paint. The marker portion is imaged after the marker portion is irradiated with illumination light, and a position of the leaf is recognized by a position of the recognition mark in a captured image. PTL 2 describes the multileaf collimator in which a reflector is provided on a leaf. Laser light is emitted toward the reflector, laser light reflected by the reflector is imaged, and a position of the leaf is recognized by a position of the reflector in a captured image. PTL 3 describes that a shape of the entire end surface is analyzed based on an image obtained by imaging the entire end surface of a leaf block (assembly), and a position of each leaf is recognized.

CITATION LIST

Patent Literature

PTL 1: WO2015/107660
PTL 2: US2013/00003080
PTL 3: JP2010-104452A

SUMMARY OF INVENTION

Technical Problem

In recent years, treatment of irradiating a small region of an affected part with radiation rays has been performed. Therefore, it is considered that the number of leaves is increased by thinning the leaves, and the shape of the passage region can be finely adjusted. However, when the leaf is thinned, it may be difficult to form a structure for detecting the position in the leaf. For example, it may be difficult to provide the marker portion as described in PTL 1 or the reflector as described in PTL 2. In the multileaf collimator described in PTL 3, when the leaf is thinned, it may be difficult to recognize the position of each leaf when a resolution of the image obtained by imaging the entire end surface of the leaf block is insufficient.

An object of the invention is to obtain a position of each leaf with high accuracy by a configuration that is easy to be manufactured in a multileaf collimator.

Solution to Problem

A multileaf collimator according to the invention includes a plurality of leaves. A collimated end surface facing radiation rays among surrounding end surfaces of each of the leaves is configured to adjust a state of the radiation rays. A reflection surface reflecting light emitted from a light source is formed on a peripheral end surface other than the collimated end surface among the surrounding end surfaces of each of the leaves.

A radiation therapy device according to the invention includes: a radiation irradiation unit configured to emit radiation rays; and a multileaf collimator including a plurality of leaves. A collimated end surface facing the radiation rays among surrounding end surfaces of each of the leaves is configured to adjust a state of the radiation rays. A reflection surface reflecting light emitted from a light source is formed on a peripheral end surface other than the collimated end surface among the surrounding end surfaces of each of the leaves.

Advantageous Effects of Invention

According to the invention, a position of each leaf can be obtained with high accuracy by a configuration that is easy to be manufactured.

BRIEF DESCRIPTION OF DRAWINGS

FIG. 1 is a diagram showing a configuration of an irradiation nozzle.

FIG. 2 is a diagram showing a configuration of the irradiation nozzle.

FIG. 3 shows a configuration of a leaf drive device and a leaf assembly.

FIG. 4 is a diagram showing an example of a leaf in which guides are formed on upper and lower edges.

FIG. 5 is a diagram showing a leaf according to a first applied embodiment.

FIG. 6 is an enlarged view of a periphery of an offset region.

FIG. 7 is a diagram schematically showing light reflected by a first reflection surface and a second reflection surface.

FIG. 8 is a diagram showing a leaf according to a second applied embodiment.

FIG. 9 is a diagram showing a leaf according to a third applied embodiment.

FIG. 10 is a diagram showing a leaf according to a fourth applied embodiment.

FIG. 11 is a diagram showing a leaf according to a fifth applied embodiment.

FIG. 12 is a diagram showing a multileaf collimator according to a sixth applied embodiment.

DESCRIPTION OF EMBODIMENTS

An embodiment of the invention will be described with reference to the drawings. The same components shown in a plurality of drawings are denoted by the same signs, and the description thereof will be simplified. In the present specification, terms indicating directions such as up, down, left, and right indicate directions in the drawings. The terms indicating the directions do not limit postures when the components are disposed.

FIG. 1 shows a configuration of an irradiation nozzle 100 provided in a radiation therapy device. In FIG. 1, a direction in which radiation rays are emitted from the irradiation nozzle 100 is defined as a z-axis positive direction, and an xy plane is defined as a coordinate plane perpendicular to the z-axis. The irradiation nozzle 100 is a device that irradiates an affected part 16 with the radiation rays, and includes a radiation irradiation unit 10 and a multileaf collimator 102.

The radiation irradiation unit 10 includes a target that generates the radiation rays by collision of electrons, accelerates the electrons to collide with the target, and emits the radiation rays from the target. The radiation rays emitted by the radiation irradiation unit 10 pass through a passage region 1 of the multileaf collimator 102 (hereinafter, referred to as an MLC, and the MLC is omission of a multileaf collimator) and are emitted to the affected part 16. The MLC adjusts a state of the radiation rays emitted to the affected part 16, that is, a cross-sectional shape and spread of the radiation rays. By adjusting a shape and a size of the passage region 1 of the MLC, the affected part 16 is irradiated with the radiation rays having an appropriate cross-sectional shape and spread.

The MLC includes a pair of leaf assemblies 12L and 12R disposed on the left and right. Each leaf assembly includes a plurality of leaves 14 stacked in a thickness direction. That is, each leaf assembly includes a plurality of leaves 14 connected in the thickness direction with adjacent leaves 14 in contact with each other or spaced apart from each other. Each of the plurality of leaves 14 forming the leaf assembly 12R includes, at a left end, a collimated end surface a that draws a curve protruding to a left side. An upper lateral end surface b extends rightward from an upper end of the collimated end surface a, and a lower lateral end surface c extends rightward from a lower end thereof. Between a right end of the upper lateral end surface b and a right end of the lower lateral end surface c, there is a longitudinal end surface d extending in a longitudinal direction.

Here, the term "end surface" means a surface of an edge of the leaf 14. The end surface may include any of a flat surface, a curved surface, and an uneven surface. The collimated end surface a is an end surface that is an edge that prevents the radiation rays from traveling. The collimated end surface a may include a part of end surfaces extending in a lateral direction from upper and lower corners.

Each of the plurality of leaves 14 forming the leaf assembly 12L includes, at a right end, the collimated end surface a that draws a curve protruding to a right side. The upper lateral end surface b extends leftward from the upper end of the collimated end surface a, and the lower lateral end surface c extends leftward from the lower end thereof. Between a left end of the upper lateral end surface b and a left end of the lower lateral end surface c, there is the longitudinal end surface d extending in the longitudinal direction.

The irradiation nozzle 100 includes a leaf drive device (not shown) that moves each leaf 14 of each leaf assembly to the left and right, and each leaf 14 is movable to the left and right along a surface direction. In FIG. 2, the leaf 14 before movement is indicated by a two-dot chain line, and the leaf 14 after movement is indicated by a solid line. As shown in this drawing, a shape and a size of a cross section of the passage region 1 parallel to the xy plane are adjusted by changing a position of the leaf 14 in the surface direction to the left and right. A part of the radiation rays emitted by the radiation irradiation unit 10 collides with the collimated end surfaces a of the leaves 14, and the traveling of the radiation rays is hindered. A remaining part of the radiation rays passes through the passage region 1 and irradiates the affected part 16.

The leaf drive device provided in the irradiation nozzle 100 detects the position of the leaf 14, and moves the leaf 14 such that the detected position approaches a target position or coincides with the target position. FIG. 3 schematically shows a configuration of a leaf drive device 104 together with the leaf assembly 12R. In the following description, a configuration of the leaf assembly 12R among the pair of leaf assemblies 12L and 12R is mainly shown. The leaf assembly 12L may be formed in a substantially bilaterally symmetric manner with respect to the leaf assembly 12R. Here, the substantially bilaterally symmetrical structure includes not only a structure having a strict symmetry but also a structure in which a functional symmetry is secured and a modification is added to the extent that a function of the MLC is secured.

The leaf drive device 104 includes a light source 20, a camera 22, an analysis unit 24, and a drive mechanism 26. A reflection surface 28 is directly formed in a region on the right end of the upper lateral end surface b of the leaf 14. The reflection surface 28 may be a region of the upper lateral end surface b of the leaf 14 on which reflection processing is directly performed. The reflection processing includes processing for reducing surface roughness, such as surface polishing or mirror finishing. In order to form the reflection surface 28, paint or the like may not be necessarily used. A guide for guiding the leaf 14 in a left and right direction may be formed on a left side of the region where the reflection surface 28 is formed. The guide is a region that is higher than the region where the reflection surface 28 is formed and extends in the left and right direction, and has a shape fitted into an engagement groove that is provided in the irradiation nozzle 100 and extends in the left and right direction. An example of a detailed structure of the guide will be described later.

The light source 20 may be a light bulb, an LED, or the like. Light emitted from the light source 20 may not necessarily be coherent light. The light source 20 emits light toward the reflection surface 28 of the leaf 14. The light emitted from the light source 20 is reflected by the reflection surface 28, and a part of the reflected light travels toward the camera 22. The camera 22 serving as a light detection unit detects light reflected by the leaf 14. That is, the camera 22 captures an image of a region including the reflection surface 28 and outputs image data to the analysis unit 24. The analysis unit 24 obtains a position of the reflected light in the image indicated by the image data. The analysis unit 24 obtains the position of the leaf 14 based on the position of the reflected light obtained for the leaf 14. The position of the leaf 14 may be represented by an x-axis coordinate value of a center of gravity of the reflection surface 28.

The drive mechanism 26 includes a position sensor (not shown) that detects the position of the leaf 14. The analysis unit 24 controls the drive mechanism 26 such that the position of the leaf 14 detected by the position sensor approaches or coincides with a predetermined target position, and causes the drive mechanism 26 to move the leaf 14. The analysis unit 24 compares the position of the leaf 14 obtained based on the position of the reflected light with the position of the leaf 14 detected by the position sensor, and determines whether there is an abnormality in an operation of the position sensor.

FIG. 4 shows an example of the leaf 14 in which guides are formed on upper and lower edges. An upper guide 30 protruding upward and extending in the lateral direction is formed at an upper edge of the leaf 14. The upper lateral end surface b of the leaf 14 includes an upper surface and a side surface of the upper guide 30, and a surface of a region, other than the upper guide 30, of the upper edge of the leaf 14. Similarly, a lower guide 32 protruding downward and extending in the lateral direction is formed at a lower edge of the leaf 14. The lower lateral end surface c of the leaf 14 includes a lower surface and a side surface of the lower guide 32, and a surface of a region, other than the lower guide 32, of the lower edge of the leaf 14.

The upper guide 30 extends leftward from a position retracted toward the left side from an upper end of the longitudinal end surface d. The reflection surface 28 is formed in an offset region 34 between the upper end of the longitudinal end surface d and a right end of the upper guide 30. On the other hand, a right end of the lower guide 32 may be positioned at a lower end of the longitudinal end surface d.

An engagement groove into which the upper guide 30 is fitted and an engagement groove into which the lower guide 32 is fitted are formed in the irradiation nozzle 100. Each engagement groove extends in the lateral direction, and guides the leaf 14, to which a force is applied by the drive mechanism 26, in the lateral direction. Accordingly, the leaf 14 moves along the upper guide 30, the lower guide 32, and the engagement grooves formed in the upper and lower sides.

As described above, the MLC according to the present embodiment includes the plurality of leaves 14, and the reflection surface 28 that reflects the light emitted from the light source 20 is formed on a peripheral end surface, other than the collimated end surface a, among surrounding end surfaces of the leaf 14. The peripheral end surface includes the upper lateral end surface b, the lower lateral end surface c, and the longitudinal end surface d. That is, the peripheral end surface includes the longitudinal end surface d opposite to the collimated end surface a, and the upper lateral end surface b (lateral end surface) extending from one end of the longitudinal end surface d toward the collimated end surface a. The upper guide 30 that engages with the engagement groove for guiding the leaf 14 in the lateral direction is formed in the upper lateral end surface b. The upper guide 30 extends toward the collimated end surface a from a position retracted toward the collimated end surface a from a corner portion formed by the longitudinal end surface d and the upper lateral end surface b. The reflection surface 28 is formed in the offset region 34.

In the MLC according to the present embodiment, the reflection surface 28 is directly formed on the leaf 14. Accordingly, even when the leaf 14 is thin, the reflection surface 28 can be easily formed. In addition, even when the leaf 14 is thin, the reflection surface 28 that reliably reflects light is formed. Accordingly, the position of the leaf 14 is obtained with high accuracy. Further, when no paint is used for the reflection surface 28, there is no problem that a property of the paint changes over time due to radiation rays.

Leaves according to first to fourth applied embodiments are shown below. The leaf 14 according to the above embodiment may be replaced with a leaf according to each applied embodiment.

FIG. 5 shows a leaf 40 according to the first applied embodiment. In the leaf 40, in addition to a first reflection surface 28-1 formed in the offset region 34, a second reflection surface 28-2 is formed at the right end of the upper guide 30. FIG. 6 shows an enlarged view of a periphery of the offset region 34. The first reflection surface 28-1 is formed in the offset region 34. A sloped surface that becomes lower toward the right side is formed at the right end of the upper guide 30, and the second reflection surface 28-2 is formed on the sloped surface.

Here, the embodiment in which the leaf 40 has two reflection surfaces is shown. Three or more reflection surfaces facing different directions may be formed on the leaf. In this case, at least one of the plurality of reflection surfaces may be formed in the upper guide 30, and the rest of the plurality of reflection surfaces may be formed in the offset region 34 between the upper guide 30 and the corner portion formed by the longitudinal end surface d and the upper lateral end surface b.

FIG. 7 schematically shows light reflected by the first reflection surface 28-1 and the second reflection surface 28-2. When the leaf 40 is positioned on the left side, the light emitted from the light source 20 is reflected by the second reflection surface 28-2 and travels toward the camera 22. As indicated by the two-dot chain line, when the leaf 40 moves to the right side, the light emitted from the light source 20 is first reflected by the first reflection surface 28-1 and is incident on the second reflection surface 28-2, and is further reflected by the second reflection surface 28-2 and travels toward the camera 22.

As described above, since the second reflection surface 28-2 is provided in addition to the first reflection surface 28-1, even when the leaf 40 moves in a wide range, reflected light having a sufficient intensity is incident on the camera 22. Accordingly, a position of the leaf 40 is obtained with high accuracy over a wide range where the leaf 40 is positioned.

The leaf 40 according to the first applied embodiment may be modified to a structure in which the offset region 34 and the first reflection surface 28-1 are not provided. In this case, a rightmost end of the upper guide 30 coincides with the upper end of the longitudinal end surface d. That is, a sloped surface that becomes lower toward the right side and reaches the upper end of the longitudinal end surface d is formed on the right end of the upper guide 30, and the second reflection surface 28-2 is formed on the sloped surface. The light emitted from the light source 20 is reflected by the second reflection surface 28-2 and travels toward the camera 22. In this structure, since there is no offset region 34 between the longitudinal end surface d of the leaf 40 and the second reflection surface 28-2, highly accurate processing becomes easy.

FIG. 8 partially shows an upper right region of a leaf 42 according to the second applied embodiment. In the leaf 42, a chamfered sloped surface 44 is formed between the longitudinal end surface d and the upper lateral end surface b. The chamfered sloped surface 44 is a flat surface, which is formed between the upper end of the longitudinal end surface d and the right end of the upper lateral end surface b and faces an upper right direction. The reflection surface 28 is formed on the chamfered sloped surface 44.

FIG. 9 partially shows an upper right region of a leaf 46 according to the third applied embodiment. In the leaf 46, a protruding reflection portion 48 protruding upward is formed at an upper edge of the leaf 46. In the example shown in FIG. 9, a sloped surface 50 that becomes lower toward the right side is formed on a right side of the protruding reflection portion 48. The sloped surface 50 may be a flat surface facing the upper right. The reflection surface 28 is formed on the sloped surface 50 formed on the protruding reflection portion 48. An upper surface of the protruding reflection portion 48 may be flat, and the reflection surface may also be formed on the upper surface of the protruding reflection portion 48. Since the reflection surface is also formed on the upper surface of the protruding reflection portion 48, even when the leaf 46 moves in a wide range, reflected light having a sufficient intensity is incident on the camera 22. A shape of a sloped surface 52 on a left side of the protruding reflection portion 48 is free.

FIG. 10 partially shows an upper right region of a leaf 54 according to the fourth applied embodiment. In the leaf 54, a recessed portion 56 recessed downward is formed at an upper edge of the leaf 54. In the example shown in FIG. 10, the recessed portion 56 is formed by a first sloped surface 58, which becomes lower toward the right side and reaches a lowermost portion, and a second sloped surface 60, which becomes higher rightward from the lowermost portion. The first sloped surface 58 may be a flat surface facing the upper right, and the second sloped surface 60 may be a flat surface facing the upper left. The reflection surface 28 is formed on the first sloped surface 58. A reflection surface may also be formed on the second sloped surface 60. Since the reflection surface is also formed on the second sloped surface 60, even when the leaf 54 moves in a wide range, reflected light having a sufficient intensity is incident on the camera 22.

FIG. 11 partially shows an upper right region of a leaf 62 according to a fifth applied embodiment. In the leaf 62, a recessed curved surface 64 is formed between the upper end of the longitudinal end surface d and the upper lateral end surface b. The recessed curved surface 64 is a curved surface curved along an outer peripheral direction of the leaf 62, and is recessed in a lower left direction. The reflection surface 28 is formed on the recessed curved surface 64. The reflection surface 28 reflects incident light in all directions. That is, it can be said that the reflection surface 28 can direct light incident from all directions toward the camera 22. Accordingly, since the reflection surface 28 is formed on the recessed curved surface 64, even when the leaf 62 moves in a wide range, reflected light having a sufficient intensity is incident on the camera 22.

In the second to fifth applied embodiments respectively shown in FIGS. 8 to 11, the upper guide 30 may be formed on the upper edge of the leaf. Further, an additional reflection surface may be formed on the right end of the upper guide 30. Since the additional reflection surface is formed, even when the leaf moves in a wide range, reflected light having a sufficient intensity is incident on the camera 22.

FIG. 12 shows an MLC according to a sixth applied embodiment. FIG. 12 shows a cross section that appears when the MLC is cut along a plane parallel to a yz plane and passing through the reflection surface 28 of the leaf 14. The reflection surface 28 formed on the leaf 14 forms a recessed surface which is recessed when viewed from the camera 22 as the light detection unit. Here, a cross section of the recessed surface may be approximate to a curve by connecting straight lines formed by the reflection surfaces 28. FIG. 12 shows an optical path 70 of the light reflected by the reflection surface 28 formed on the leaf 14. The light emitted from the light source and reflected by the leaf 14 travels toward the camera 22. The leaf 14 may be replaced with any one of the leaves 40, 42, 46, 54, and 62 according to the first to fifth applied embodiments.

According to such a configuration, the reflected light is directed to a narrow range between the camera 22 and the MLC as compared with a case where the reflection surfaces 28 of the plurality of leaves 14 are disposed flat. Accordingly, a distance between the camera 22 and the MLC is shortened, and the irradiation nozzle 100 is downsized. Alternatively, a camera having a narrow viewing angle and a large number of pixels per unit solid angle can be used.

In each of the above embodiments, the reflection surface is formed near a corner of the leaf, that is, at an end of the upper lateral end surface b. The reflection surface may be formed at an intermediate position of the upper lateral end surface b. In the leaf in each embodiment, a reflectance reducing processed surface may be formed in a region other than the reflection surface. The reflectance reducing processed surface may be a surface having a surface roughness larger than a predetermined roughness and diffusing incident light in all directions.

The reflectance reducing processed surface may be a surface covered with a material having a color such as black that hardly reflects light. For example, among the upper lateral end surface b and the longitudinal end surface d of the leaf shown in each drawing, an end surface other than the reflection surface may be the reflectance reducing processed surface. In the leaf shown in FIG. 6, in particular, among the longitudinal end surface d and the upper lateral end surface b, end surfaces, other than the first reflection surface 28-1 and the second reflection surface 28-2, may be the reflectance reducing processed surfaces. Further, a surface (front surface or rear surface) perpendicular to a y-axis of the leaf may be the reflectance reducing processed surface. By providing the reflectance reducing processed surface, a contrast of an image captured by the camera 22 is increased. Accordingly, processing of obtaining the position of the reflected light and obtaining the position of the leaf is facilitated.

REFERENCE SIGNS LIST

1: passage region
10: radiation irradiation unit
12L, 12R: leaf assembly
14, 40, 42, 46, 54, 62: leaf
16: affected part
20: light source
22: camera (light detection unit)
24: analysis unit
26: drive mechanism
28: reflection surface
28-1: first reflection surface
28-2: second reflection surface
30: upper guide
32: lower guide
34: offset region
44: chamfered sloped surface
50, 52: sloped surface
58: first sloped surface
60: second sloped surface
64: recessed curved surface
70: optical path
100: irradiation nozzle
102: multileaf collimator (MLC)
104: leaf drive device a: collimated end surface
b: upper lateral end surface
c: lower lateral end surface
d: longitudinal end surface

The invention claimed is:

1. A multileaf collimator comprising:
a plurality of leaves,
wherein a collimated end surface facing radiation rays among surrounding end surfaces of each of the leaves is configured to adjust a state of the radiation rays,
wherein a reflection surface reflecting light emitted from a light source is directly formed on a peripheral end surface of the leaf other than the collimated end surface among the surrounding end surfaces of each of the leaves, and
wherein the reflection surface is a region where the peripheral end surface is subjected to reflection processing.

2. The multileaf collimator according to claim 1,
wherein the peripheral end surface includes a longitudinal end surface opposite to the collimated end surface and a lateral end surface extending from one end of the longitudinal end surface toward the collimated end surface,
wherein the lateral end surface is formed with a guide that engages with an engagement groove for guiding the leaf in a lateral direction and that extends in the lateral direction, and
wherein the reflection surface is formed on the guide.

3. The multileaf collimator according to claim 1,
wherein the peripheral end surface includes a longitudinal end surface opposite to the collimated end surface and a lateral end surface extending from one end of the longitudinal end surface toward the collimated end surface,
wherein the lateral end surface is formed with a guide that engages with an engagement groove for guiding the leaf in a lateral direction and that extends, toward the collimated end surface, from a position retracted toward the collimated end surface from a corner portion formed by the longitudinal end surface and the lateral end surface, and
wherein the reflection surface is formed in an offset region between the corner portion and the guide.

4. The multileaf collimator according to claim 1,
wherein a plurality of the reflection surfaces facing different directions are formed on the peripheral end surface.

5. The multileaf collimator according to claim 4,
wherein the peripheral end surface includes a longitudinal end surface opposite to the collimated end surface and a lateral end surface extending from one end of the longitudinal end surface toward the collimated end surface,
wherein the lateral end surface is formed with a guide that engages with an engagement groove for guiding the leaf in a lateral direction and that extends, toward the collimated end surface, from a position retracted toward the collimated end surface from a corner portion where the longitudinal end surface and the lateral end surface are in contact with each other,
wherein at least one of the plurality of reflection surfaces is formed in the guide, and
wherein a rest of the plurality of reflection surfaces is formed in an offset region between the corner portion and the guide.

6. The multileaf collimator according to claim 1,
wherein the reflection surface is a curved surface curved along an outer peripheral direction of the leaf.

7. The multileaf collimator according to claim 1,
wherein the reflection surface formed on each of the leaves forms a recessed surface that is recessed when viewed from a light detection unit that detects light reflected by the leaf.

8. The multileaf collimator according to claim 1,
wherein a reflectance reducing processed surface is formed in a region other than the peripheral end surface.

9. A radiation therapy device comprising:
the multileaf collimator according to claim 1;
a radiation irradiation unit configured to emits the radiation rays;
a light detection unit configured to detect light reflected by each of the leaves; and
an analysis unit configured to obtain a position of each of the leaves based on the light detected by the detection unit.

10. A radiation therapy device comprising:
a radiation irradiation unit configured to emit radiation rays; and
a multileaf collimator including a plurality of leaves,
wherein a collimated end surface facing the radiation rays among surrounding end surfaces of each of the leaves is configured to adjust a state of the radiation rays,
wherein a reflection surface reflecting light emitted from a light source is directly formed on a peripheral end surface of the leaf other than the collimated end surface among the surrounding end surfaces of each of the leaves, and
wherein the reflection surface is a region where the peripheral end surface is subjected to reflection processing.

11. The multileaf collimator according to claim 1,
wherein the reflection surface is polished.

12. The multileaf collimator according to claim 1,
wherein the reflection surface has a mirror surface.

* * * * *